(12) United States Patent
Hirokawa et al.

(10) Patent No.: US 8,716,186 B2
(45) Date of Patent: May 6, 2014

(54) AGRICULTURAL AND HORTICULTURAL WATER DISPERSIBLE GRANULE

(75) Inventors: Takashi Hirokawa, Sakura (JP); Takashi Gotou, Izumiotsu (JP); Ichirou Urihara, Odawara (JP)

(73) Assignee: Nippon Soda Co., Ltd., Tokyo (JP)

( * ) Notice: Subject to any disclaimer, the term of this patent is extended or adjusted under 35 U.S.C. 154(b) by 638 days.

(21) Appl. No.: 10/543,039

(22) PCT Filed: Jan. 21, 2004

(86) PCT No.: PCT/JP2004/000491
§ 371 (c)(1),
(2), (4) Date: Feb. 14, 2006

(87) PCT Pub. No.: WO2004/064518
PCT Pub. Date: Aug. 5, 2004

(65) Prior Publication Data
US 2006/0189485 A1    Aug. 24, 2006

(30) Foreign Application Priority Data

Jan. 23, 2003 (JP) .................................. 2003-14640

(51) Int. Cl.
*A01N 25/12* (2006.01)
*A01N 25/00* (2006.01)

(52) U.S. Cl.
USPC .......................................... 504/367; 424/405

(58) Field of Classification Search
None
See application file for complete search history.

(56) References Cited

U.S. PATENT DOCUMENTS

| | | | | |
|---|---|---|---|---|
| 4,511,395 A | * | 4/1985 | Misselbrook | 504/347 |
| 4,600,433 A | * | 7/1986 | Alt | 504/340 |
| 4,701,210 A | * | 10/1987 | Tanaka et al. | 504/322 |
| 5,523,276 A | * | 6/1996 | Suzuki et al. | 504/136 |
| 5,945,114 A | * | 8/1999 | Ogawa et al. | 424/408 |
| 6,908,882 B1 | * | 6/2005 | Becher et al. | 504/116.1 |
| 2004/0266626 A1 | * | 12/2004 | Schrof et al. | 504/361 |

FOREIGN PATENT DOCUMENTS

| | | |
|---|---|---|
| EP | 1407665 A1 | 4/2004 |
| JP | 55-64505 A | 5/1980 |
| JP | 3-163006 | 7/1991 |
| JP | 8319201 | 12/1996 |
| JP | 2000-72602 | 3/2000 |
| JP | 2000-204003 | 7/2000 |
| JP | 2000-256109 A | 9/2000 |
| JP | 2003-315295 A | 11/2003 |
| WO | WO 99/40162 A1 | 8/1999 |
| WO | 02102152 A1 | 12/2002 |

OTHER PUBLICATIONS

Pesticide Formulation Guide, *Japan Plan Protection Association*, (1997).
Translation of Notice of Allowance mailed Nov. 4, 2009 in corresponding Japanese patent application 2004-011758.
Supplementary European Search Report dated Jun. 1, 2011, in corresponding EP 04 70 3921, 4 pages.
XP002635604, Database WPI, Week 198026, AN 1980-45565C (Abstract of JP 55-064505) 1980, 2 pages.
XP002635602, Database CA [Online], Chem. Abst. Service, 2000, (Abstract of JP 2000-256109), Database accession No. 133:233911, 2000, 3 pages.
XP00263603, Database WPI, Week 200067, AN 2000-682074 (Abstract of JP 2000-256109), 2000, 3 pages.
XP002635603, Database WPI, Week 200067, AN 2000-682074 (Abstract of JP 2000-256109), 2000, 3 pages.

* cited by examiner

*Primary Examiner* — Tracy Vivlemore
*Assistant Examiner* — Monica Shin
(74) *Attorney, Agent, or Firm* — Foley & Lardner LLP

(57) ABSTRACT

An object of the present invention is to provide an agricultural and horticultural water dispersible granule, which shows excellent properties of disintegrating and dispersing after being put into water, and which does not cause phytotoxicity, even in the case wherein an agricultural chemical technical product having a melting or softening point of 70° C. or below, the formulation of which into water dispersible granules was difficult in the prior art, is used. The agricultural and horticultural water dispersible granule is produced by granulating a mixture containing an agricultural chemical technical product having a melting or softening point of 70° C. or below, a salt of N-acylamino acid, and an adsorbent carrier. The agricultural and horticultural water dispersible granules as described above which further contain at least one of a formaldehyde condensate of aromatic sulfonate and a lignosulfonate. The agricultural and horticultural water dispersible granules as described above which further contain N-acylmethyltaurate.

12 Claims, No Drawings

AGRICULTURAL AND HORTICULTURAL WATER DISPERSIBLE GRANULE

RELATED APPLICATIONS

This application is a 35 U.S.C. 371 national stage filing of International Application No. PCT/JP2004/000491, filed 21 Jan. 2004, which claims priority to Japanese Patent Application No. 2003-014640 filed on 23 Jan. 2003 in Japan. The contents of the aforementioned applications are hereby incorporated by reference.

TECHNICAL FIELD

This invention relates to an agricultural and horticultural water dispersible granule which can disintegrate and disperse immediately after being put into water.

BACKGROUND ART

Conventional water dispersible granules are produced by mixing and grinding agricultural chemical technical products, and wetting agents, dispersants, and fillers. However, these water dispersible granules have problems. For example, the water dispersible granules have a small apparent specific gravity and increased volume, because the water dispersible granules contain finely pulverized powders of the agricultural chemical technical products and inorganic minerals, and the water dispersible granules are not preferable for maintaining health of workers, because the fine powders become dusty when suspending the fine powders in water to prepare spray solution, and, they require much time to be measured, because they are fine powders, and so various attempts have been recently made to develop water dispersible granules in which the water dispersible granules are granulated.

Water dispersible granules are produced by mixing, grinding and granulating agricultural chemical technical products, wetting agents, dispersants, binders, and other inert ingredients, as needed. Because the water dispersible granules are required to disintegrate and disperse immediately after being put into water, various contrivances have been attempted to enable the granules to disintegrate and disperse. Methods of producing agricultural and horticultural water dispersible granules have been reported, by which, for example, formaldehyde condensate of alkylnaphthalene sulfonates, lignosulfonates, polyacrylates, alkylaryl sulfonates, polycarboxylates, polyoxyethylene polyoxypropylene block polymers, polystyrene polyoxyethylene block polymers, or the like, are used as a dispersant, and sodium alkylnaphthalenesulfonates, sodium alkylsulfates, sodium alkylbenzenesulfonates, sodium alkylsulfosuccinates, polyoxyethylene alkylarylethers, or the like, are used as a wetting agent (for example, Non-patent Document 1).

In regard to methods of producing agricultural and horticultural water dispersible granules using agricultural chemical technical products liquid at room temperature or having a low melting point, which are difficult to produce, formulation methods have been proposed in which the agricultural chemical technical products liquid at room temperature or having a low melting point are mixed with a great deal of inactive material, or in which the agricultural chemical technical products are dissolved in a solvent to be adsorbed by adsorbent carriers (for example, Non-patent Document 1).

However, even when these methods are used, it is difficult to produce water dispersible granules having good disintegrability and dispersibility in water by using agricultural chemical technical products having a melting or softening point of 70° C. or below, although the cause is unknown. Therefore, a method of producing water dispersible granules by, for example, mixing agricultural chemical technical products having a melting point of 70° C. or below with calcined silica produced by wet process and dispersants has been proposed as an improved method of producing water dispersible granules (see, for example, Patent Document 1).

However, according to this method, water dispersible granules having sufficient disintegrability and dispersibility cannot be produced when using agricultural chemical technical products of which the melting or softening point is 70° C. or below.

Non-patent Document 1: Pesticide Science Society of Japan, Pesticide Formulation Guide, edited by Japan Agricultural Formulation and Application Symposium, issued by the Japan Plant Protection Association, Oct., 30th, 1997, p. 22 to 24.

Patent Document 1: Japanese Patent Application, First Publication No. Hei 3-163006

DISCLOSURE OF THE INVENTION

Problems To Be Solved By The Invention

An object of the present invention is to provide an agricultural and horticultural water dispersible granule having excellent underwater disintegrability and dispersibility without phytotoxicity, when using an agricultural chemical technical product of which the melting or softening point is 70° C. or below.

Means For Solving The Problem

As a result of various studies in respect to effects of the structure of dispersants exerted on underwater disintegrability and dispersibility of water dispersible granules, the inventors of the present invention found that water dispersible granules having excellent underwater disintegrability and dispersibility can be produced by granulating a mixture of an agricultural chemical technical product having a melting or softening point of 70° C. or below, a salt of N-acylamino acid used as a dispersant, and an adsorbent carrier. Although salts of N-acylamino acids have been conventionally used in cleaner creams or the like as surfactants having low irritating properties and high safety properties, there are no other examples in which the salts of N-acylamino acids are used to produce water dispersible granules. A combination of a particular dispersant, that is, a salt of N-acylamino acid, and an agricultural chemical technical product having a melting or softening point of 70° C. or below, exerts significant effects in achieving the object of the present invention.

The present invention has been completed based on these findings.

That is, the present invention provides an agricultural and horticultural water dispersible granule comprising an agricultural chemical technical product of which melting or softening point is 70° C. or below, a salt of N-acylamino acid, and an adsorbent carrier.

Moreover, the present invention provides the agricultural and horticultural water dispersible granules as described above further including at least one of formaldehyde condensate of aromatic sulfonates and lignosulfonates.

Moreover, the present invention provides the agricultural and horticultural water dispersible granules as described above further comprising an N-acylmethyltaurate.

BEST MODE FOR CARRYING OUT THE INVENTION

<Agricultural Chemical Technical Products>

As the agricultural chemical technical products used in the agricultural and horticultural water dispersible granule of the present invention, any compounds generally used as agricultural chemicals, such as fungicides, herbicides, plant growth regulators, or the like, can be used, provided that they have melting or softening points of 70° C. or below, and these compounds may be used alone or may be used as a mixture of two or more.

Examples of agricultural chemical technical products having a melting point of 70° C. or below include: N-1,2-dimethylpropyl)-N'ethyl-6(methylthio)-1,3,5triazine-2,4diamine (common name: dimethametryn, melting point: 65° C.), S,S'-dimethyl-2-(difluoromethyl)-4(2-methylpropyl)-6-(trifluoromethyl)-3,5pyridinedicarbothionate (common name: dithiopyr, melting point: 65° C.), 2,3-dihydro-3,3dimethyl-5benzofuranyl ethanesulfonate (common name: benfuresate, melting point: 32 to 35° C.), butyl(R)-2-[4-(4-cyano-2-fluorophenoxy)phenoxy]propyonate (common name: cyhalofop-butyl, melting point: 50° C.), S-1-methyl-1phenylethyl piperidine-1-carbothioate (common name: dimepiperate, melting point: 38.8 to 39.3° C.), and the like. Examples of agricultural chemical technical products which are liquid at room temperature include 2-chloro-2',6'-diethyl-N-(2-propoxyethyl)-acetanilide (common name: pretilachlor), S-benzyl-N-(1,2-dimethylpropyl)-N-ethylthiocarbamate (common name: esprocarb), and the like.

Examples of agricultural chemical technical products having a softening point of 70° C. or below include 1,1'-iminodi(octamethylene)diguanidium=tris(alkylbenzene sulfonate) (common name: iminoctadine albesilate, softening point: 55 to 60° C.), and the like.

The agricultural and horticultural water dispersible granule according to the present invention may furhter include an agricultural chemical technical product of which the melting or softening point is over 70° C. Examples of such agricultural chemical technical products include 2-isopropylphenyl-N-methylcarbamate (common name: MIPC, melting point: 88 to 93° C.), 3,5-xylyl-N-methylcarbamate (common name: XMC, melting point: 99 to 100° C.), (RS)-5-tert-butyl-2[2-(2,6-difluorophenyl)-4,5dihydro-1,3oxazole-4yl]phenetole (common name: etoxazole, melting point: 101 to 102° C.), O-3-tert-butylphenyl-6-methoxy-2-pyridyl(methyl)thiocarbamate (common name: pyributicarb, melting point: 85.7 to 86.2° C.), methyl 5-(2,4-dichlorophenoxy)-2-nitrobenzoate (common name: biphenox, melting point: 84 to 86° C.), 1-(α,α-dimethylbenzyl)-3-p-tolylurea (common name: daimuron, melting point: 203° C.), N,N-diethyl-3-mesitylsulfonyl-1H-1,2,4-triazole-1-carboxamide (common name: cafenstrole, melting point: 114 to 116° C.), α-(4,6-dimethoxypyrimidin-2-ylcarbamoylsulfamoyl)-o-toluic acid (common name: bensulfuron-methyl, melting point: 185 to 188° C.), 2-bromo-N-(α,α-dimethylbenzyl)-3,3-dimethylbutanamide (common name: bromobutide, melting point: 180.1° C.), 1-(2-chloroimidazo[1,2-a]pyridin-3-ylsulfonyl)-3-(4,6-dimethoxypyridine-2-yl)urea (common name: imazosulfuron, melting point: 183 to 184° C.), 1-[2(cyclopropylcarbonyl)phenylsulfamoyl]-3(4,6-dimethoxypyrimidin-2yl)-urea (common name: cyclosulfamuron, melting point: 149.6 to 153.2° C.), methyl (E)-2-methoxyimino[2-(o-tolyloxymethyl)phenyl] acetate (common name: kresoxim-methyl, melting point: 101.6 to 102.5° C.), methyl (E)-2-{2-[6-(2-cyanophenoxy)pyrimidin-4-yloxy]phenyl}-3methoxyacrylate (common name: azoxystrobin, melting point: 116° C.), 5-[[2-amino5-O-(aminocarbonyl)-2-deoxy-L-xylonyl]amino]-1,5-dideoxy-1-[3,4-dihydro-5-(hydroxymethyl)-2,4-dioxo-1(2H)-pyrimidyl]-β-D-allofuranuronic acid (common name: polyoxine, melting point: 160°C. or above), bis(dimethylthiocarbamoyl)disulfide (common name: thiram, melting point: 155 to 156° C.), N-(2,3-dichloro-4-hydroxyphenyl)-1-methylcyclohexanecarboxamide (common name: fenhexamid, melting point: 153° C.), manganese ethylenebis(dithiocarbamate) (polymeric) complex with zinc salt (common name: mancozeb, melting point: 192° C. or above), 3-(3,5-dichlorophenyl)-N-isopropyl-2,4-dioxoimidazolydine-1-carboxamide (common name: iprodione, melting point: 134° C.), 3'-isopropoxy-2-methylbenzanilide (common name: mepronil, melting point: 92 to 93° C.) (1RS, 2SR, 5SR; 1RS, 2S, 5SR)-2-(4-chlorobenzyl)-5-isopropyl-1-(1H-1,2,4-triazole-1-ylmethyl)cyclopentanol (common name: ipconazole, melting point: 91 to 119° C.), and the like.

<Salt of N-acylamino Acid>

The salt of N-acylamino acid used in the agricultural and horticultural water dispersible granule according to the present invention is an anionic surfactant synthesized by using an amino acid as the main raw material thereof, and is used as a dispersant of the water dispersible granule. An acyl group of the salt of N-acylamino acid preferably has 8 to 24 carbon atoms, and examples of such acyl group include a lauroyl group, a myristoyl group, a stearoyl group, and the like.

Examples of amino acids of salts of N-acylamino acid include glycine, sarcosine, alanine, valine, leucine, lysine, arginine, glutamic acid, aspartic acid, methionine, cystine, cysteine, phenylalanine, and the like, and examples of salts thereof include physiologically acceptable salts, such as salts of alkaline metals such as sodium, potassium, lithium, and the like, salts of alkaline earth metals such as magnesium, calcium, and the like, salts of acids such as hydrochloric acid, sulfuric acid, and the like, salts of amines such as ammonia, triethanolamine, triethylamine, and the like.

Specific examples of salts of N-acylamino acid and commercial items thereof include trade names "Amisoft HS-11" (sodium N-stearoyl-L-glutamate), "Amisoft HS-21" (disodium N-stearoyl-L-glutamate), "Amisoft CS-11" (sodium N-coconut oil fatty acid acyl-L-glutamate), "Amisoft LS-11" (sodium N-lauroyl-L-glutamate), and "Amisoft MS-11" (sodium N-myristoyl-L-glutamate), which are manufactured by AJINOMOTO Co., Inc., trade names "Soypon SLP" (sodium lauroyl sarcosine) and "Alanon AMP" (sodium N-myristoyl-N-methyl-β-alanine), which are manufactured by Kawaken Fine Chemicals Co., Ltd., and the like. These salts of N-acylamino acids may be used alone, or may be used as a mixture of two or more.

Among these, trade names "Amisoft HS-11" (sodium N-stearoyl-L-glutamate), "Amisoft HS-21" (disodium N-stearoyl-L-glutamate), and "Amisoft CS-11" (sodium N-coconut oil fatty acid acyl-L-glutamate), which are manufactured by AJINOMOTO Co., Inc., and trade name "Soypon SLP" (sodium lauroyl sarcosine) manufactured by Kawaken Fine Chemicals Co., Ltd., are particularly preferable, because they can give good disintegrability and dispersibility.

<Adsorbent Carrier>

As the adsorbent carrier used in the agricultural and horticultural water dispersible granule according to the present invention, mineral fine powders having high oil absorbing property are preferably used. Although examples of adsorbent carriers produced from mineral fine powders include synthetic noncrystalline silicas, diatomaceous earths, zeolites, attapulgites, acid clays, and the like, the adsorbent carrier is not particularly limited to these. The agricultural chemical technical products may be used after being absorbed by, or being adsorbed to these adsorbent carriers, or being mixed with the adsorbent carriers. Alternatively, the agricultural chemical technical products may be dissolved in an organic solvent to be adsorbed to the adsorbent carriers.

Synthetic noncrystalline silicas which can be used as the adsorbent carrier are called hydrosilicic acids, wet silicas, synthetic silicic acids, or the like, and have a Si—O network structure without uniform crystalline structure. Examples of commercial items of the synthetic noncrystalline silicas include trade names "CARPLEX #80", "CARPLEX XR", "CARPLEX FPS-3", "CARPLEX CS-8" (calcined synthetic noncrystalline silica), and "CARPLEX BS-304" (synthetic noncrystalline silica, gel type), which are manufactured by SHIONOGI & CO., LTD., trade names "Nipsil NS-K", and "Nipsil NS-KR", which are manufactured by NIPPON SILICA CORPORATION, trade names "Tokusil NSK", and "Tokusil P", which are manufactured by Tokuyama Corporation, and the like.

Diatomaceous earths which can be used as the adsorbent carrier are porous stones or soils which exist in strata formed by relict shells mainly consisting of silicic acids produced by degradation of protoplasms of diatoms which are unicellular algae, and which are deposited on sea bottoms or lake bottoms, and the diatomaceous earths are formed by aggregates of porous shells having the shape of a circle, a needle, a boat, or the like, generally contain 80% or more of silicic acid moieties ($SiO_2$), and mainly consist of noncrystalline silicic acids. Although there are no particular limitations imposed on the diatomaceous earths used as the adsorbent carrier, examples of commercial items thereof include trade name "Zemlite 3Y" manufactured by Hakusan Corporation, trade name "Radiolite" manufactured by Showa Chemical Industry Co., Ltd., and the like.

Zeolites which can be used as the adsorbent carrier are hydrated aluminosilicates of alkalis or alkaline earth metals, and have fine pores in the crystals thereof. Although there are no particular limitations imposed on the zeolites used as the adsorbent carrier, examples of commercial items thereof include trade name "NITTO Zeolite #150" manufactured by NITTO FUNKA KOGYO KK., trade name "Izumo Zeolite" manufactured by KASANENKOGYO KK., and the like.

Attapulgites which can be used as the adsorbent carrier are hydrated magnesium aluminum silicate minerals. Although there are no particular limitations imposed on the attapulgites used as the adsorbent carrier, examples of commercial items thereof include trade names "Microsorb 300 LVM", and "Microsorb 300 RVM", which are manufactured by Engelhard Corporation, and the like.

Although there are no particular limitations imposed on acid clays used as the adsorbent carrier, examples of commercial items thereof include trade name "MIZUKA-ACE #200" manufactured by MIZUSAWA INDUSTRIAL CHEMICALS, LTD., and the like. Activated clays which are clay minerals mainly consisting of montmorillonite may also be used without particular limitation as the adsorbent carrier of the agricultural and horticultural water dispersible granule according to the present invention.

Among these mineral fine powders, the synthetic noncrystalline silicas and the diatomaceous earths are preferably used, because they are easily obtained.

<Formaldehyde Condensates of Aromatic Sulfonates and Lignosulfonates>

It is preferable to use as a wetting agent at least one of formaldehyde condensates of aromatic sulfonates and lignosulfonates for the purpose of further improving wettability of the agricultural and horticultural water dispersible granule according to the present invention. These wetting agents may be used alone, or may be used as a mixture of two or more.

Although there are no particular limitations imposed on the formaldehyde condensates of aromatic sulfonates available for the agricultural and horticultural water dispersible granule according to the present invention, examples of commercial items thereof include trade names "DEMOL SNB" (formaldehyde condensate of sodium aromatic sulfonate), "DEMOL MS" (formaldehyde condensate of sodium aromatic sulfonate), "DEMOL N" (formaldehyde condensate of sodium naphthalene sulfonate), "DEMOL RN" (formaldehyde condensate of sodium naphthalene sulfonate), and "DEMOL T" (formaldehyde condensate of sodium naphthalene sulfonate), which are manufactured by Kao Corportaion, trade names "SUPRAGIL NMS/90" (formaldehyde condensate of sodium methyl naphthalene sulfonate), and "SUPRAGIL RM/210-EI" (formaldehyde condensate of sodium alkylnaphthalene sulfonate), which are manufactured by RHODIA NICCA LTD., trade names "NEWKALGEN PS-P" (formaldehyde condensate of sodium alkylnaphthalene sulfonate), "NEWKALGEN 207" (formaldehyde condensate of sodium naphthalenesulfonate), and "NEWKALGEN WG-2" (formaldehyde condensate of sodium naphthalenesulfonate), which are manufactured by Takemoto Oil & Fat Co., Ltd., trade name "Runox 1000 C"(formaldehyde condensate of sodium naphthalenesulfonate) manufactured by TOHO Chemical Industry Co., LTD., trade name "Disrol SH" (formaldehyde condensate of sodium naphthalenesulfonate) manufactured by Nippon Nyukazai Co., Ltd., trade names "Lavelin FA" (formaldehyde condensate of sodium naphthalenesulfonate), and "Lavelin FW" (formaldehyde condensate of sodium naphthalenesulfonate), which are manufactured by DAI-ICHI KOGYO SEIYAKU CO., LTD., and the like.

Examples of commercial items of the lignosulfonates available for the water dispersible granule according to the present invention include trade names "SANX P252"(sodium lignosulfonate), "SANX P201" (calcium lignosulfonate), "VANILLEX N" (partially desulfonated sodium lignosulfonate), "VANILLEX RN" (partially desulfonated sodium lignosulfonate), "PEARLLEX NP" (high molecular weight sodium lignosulfonate), and "PEARLLEX DP" (modified sodium lignosulfonate), which are manufactured by Nippon Paper Group, Inc., trade names "NEWKALGEN RX-B" (sodium lignosulfonate), "NEWKALGEN RX-C" (sodium lignosulfonate), and "NEWKALGEN WG-4" (sodium lignosulfonate), which are manufactured by Takemoto Oil & Fat Co., Ltd., trade name "Sorpol 9047K" (sodium lignosulfonate) manufactured by TOHO Chemical Industry Co., LTD., trade name "SUPRAGIL L/393" (calcium lignosulfonate) manufactured by RHODIA NICCA LTD., and the like.

<N-acyhnethyltaurate>

When the agricultural and horticultural water dispersible granule according to the present invention is used, it requires water as a diluted solution. When the water is containing a great deal of Ca ions, Mg ions, or the like, that is, hard water, the ions may decrease dispersibility of the water dispersible granules. The above-mentioned problem can be solved by using N-acylmethyltaurates in the agricultural and horticultural water dispersible granule according to the present invention.

N-acylmethyltaurate has a structure remarkably similar to that of a taurocholic acid which is an intravital surfactant existing in bile of human and animals, is an anionic surfactant having low irritating properties and high safety properties, and is conventionally used in shampoo bases, creams, and the like. When the agricultural and horticultural water dispersible granule containing N-acylmethyltaurate according to the present invention is dispersed in hard water containing a great deal of Ca and Mg, it exerts excellent disintegrability and dispersibility in water without being effected by the many Ca ions or the like.

An acyl group of the N-acylmethyltaurate preferably has 8 to 24 carbon atoms, and examples thereof include a lauroyl group, a myristoyl group, a stearoyl group, and the like.

Examples of salts of N-acylmethyltaurates include physiologically acceptable salts, such as salts of alkaline metals such as sodium, potassium, or lithium, salts of alkaline earth metals such as magnesium, or calcium, salts of inorganic acids such as hydrochloric acid, sulfiric acid, or the like, salts of amines such as ammonia, triethanolamine, or triethylamine, or the like.

Specific examples of N-acylmethyltaurate and commercial items thereof include trade names "NIKKOL LMT" (sodium N-lauroyl methyl taurate), "NIKKOL MMT" (sodium N-myristoyl methyl taurate), "NIKKOL PMT" (sodium N-palmitoyl methyl taurate), "NIKKOL SMT" (sodium N-stearoylmethyl taurate), and "NIKKOL CMT-30" (sodium N-coconut oil fatty acidmethyl taurate), which are manufactured by Nikko Chemicals co., ltd., trade name "Marpon T" (sodium N-oleylmethyl taurate) manufactured by Matsumoto Yushi-Seiyaku Co., Ltd., trade name "LIPOTAC TE" (sodium N-stearoylmethyl taurate) manufactured by Lion Corporation., trade name "DIAPON K-MG" (magnesium N-coconut oil fatty acidmethyl taurate), and "DIAPON K-SF" (sodium N-coconut oil fatty acidmethyl taurate), which are manufactured by NOF CORPORATION, and the like. These N-acylmethyltaurates may be used alone, or may be used as a mixture of two or more.

In the agricultural and horticultural water dispersible granules according to the present invention, the agricultural chemical technical product is contained in an amount of 10 to 60% by mass, preferably 20 to 50% by mass, the N-acylamino acid is contained in an amount of 10 to 30% by mass, more preferably 20 to 30% by mass, and the adsorbent carrier is contained in an amount of 10 to 80% by mass, more preferably 20 to 60% by mass.

When at least one of aromatic formaldehyde condensates and lignosulfonates is further contained in the agricultural and horticultural water dispersible granule according to the present invention, the proportion of the aromatic formaldehyde condensates and the lignosulfonates is preferably 5 to 25% by mass, relative to the total mass of the agricultural chemical technical product, the N-acylamino acid, the adsorbent carrier, the formaldehyde condensates of aromatic sulfonates, and the lignosulfonates.

Specifically, the proportion of the agricultural chemical technical product is 10 to 55% by mass, more preferably 20 to 50% by mass, the proportion of the N-acylamino acid is 5 to 20% by mass, more preferably 10 to 15% by mass, the proportion of the adsorbent carrier is 5 to 80% by mass, more preferably 20 to 60% by mass, and the proportion of the aromatic formaldehyde condensates and the lignosulfonates is 5 to 25% by mass, more preferably 10 to 20% by mass.

When the agricultural and horticultural water dispersible granule according to the present invention further contains the N-acylmethyltaurate, the proportion of the N-acylmethyltaurate is preferably 0.5 to 10% by mass, relative to the total mass of the agricultural chemical technical product, the N-acylamino acids, the adsorbent carrier, the formaldehyde condensates of aromatic sulfonate, the lignosulfonates, and the N-acyltaurate.

Specifically, the proportion of the agricultural chemical technical product is 10 to 55% by mass, more preferably 20 to 50% by mass, the proportion of the N-acylamino acid is 5 to 20% by mass, more preferably 10 to 15% by mass, the proportion of the adsorbent carrier is 5 to 79.5% by mass, more preferably 20 to 59% by mass, the proportion of the aromatic formaldehyde condensates and the lignosulfonates is 5 to 25% by mass, more preferably 10 to 20% by mass, and the proportion of the N-acylmethyltaurates is 0.5 to 10% by mass, more preferably 1 to 5% by mass.

In the agricultural and horticultural water dispersible granule according to the present invention, wetting agents other than the above-mentioned wetting agents, fillers, and binders may be included, as needed. In this case, the proportion thereof is preferably the proportion of the above-mentioned constituents within the range described above.

Examples of wetting agents other than the above-mentioned wetting agents include sodium alkylnaphthalenesulfonate, sodium alkylsulfate, sodium alkylbenzenesulfonate, sodium alkylsulfosuccinate, polyoxyethylene alkylarylether, and the like.

Examples of fillers include mica, calcium carbonate, kaolin clay, clay, bentonite, acid clay, talc, magnesium carbonate, titanium dioxide, glucose, lactose, saccharose, ammonium sulfate, sodium sulfate, urea, and the like.

Examples of binders include carboxymethyl cellulose, polyvinyl alcohol, polyvinyl pyrrolidone, dextrin, soluble starch, and the like.

Although the agricultural and horticultural water dispersible granule according to the present invention is generally dispersed in soft water in order to be sprayed, it may be dispersed in the above-mentioned hard water in some areas. Examples of hard water include CIPAC standard water D (342 ppm ($Ca^{2+}:Mg^{2+}=4:1$)) named in accordance with the CIPAC (Collaborative International Pesticide Analytical Council; Collaborative International Pesticide Analytical Council) method.

Although there are no particular limitations imposed on the form of the agricultural and horticultural water dispersible granule according to the present invention, it may have spherical, cylindrical, or irregular shape, and its size is preferably 0.1 to 5 mm at its longest portion.

<Method of Producing the Water Dispersible Granule>

Although the water dispersible granule according to the present invention may be produced in accordance with the following producing method, for example, it may be produced without being limited to this method.

<Method of Producing the Water Dispersible Granule Using an Agricultural Chemical Technical Product Having a Melting Point of 70° C. or Below>

When an agricultural chemical technical product having a melting point of 70° C. or below is used, both the agricultural chemical technical product liquefied by heating at its melting point or above and the adsorbent carrier, or, both a solution in which the agricultural chemical technical product is dissolved in a volatile solvent or a nonvolatile solvent and the adsorbent carrier, are mixed by using a mixer such as, for example, a ribbon mixer, a Nauter mixer, a mixing granulator, or the like, to produce a powdered mixture in which the agricultural chemical technical product is adsorbed to the adsorbent carrier. In the case of using a volatile solvent, the solvent is removed by heating after mixing by means of the mixer such as a mixing granulator or the like to produce the powdered mixture.

As the volatile solvent, volatile solvents, in which the agricultural chemical technical product can be dissolved or can be homogeneously mixed, the volatile solvents being able to be removed by heating, are preferable, and examples of such volatile solvents include lower alcohols such as methanol, and ethanol, and lower ketones such as acetone, and methyl ethyl ketone. Examples of nonvolatile solvents include aromatic hydrocarbons, ketones, fatty acid esters, phthalic acid esters, vegetable oils, and the like.

When the water dispersible granule is produced by using an agricultural chemical technical product liquid at room temperature or a solution in which the agricultural chemical technical product is dissolved in a nonvolatile solvent, both the agricultural chemical technical product or the solution and the adsorbent carrier are mixed by using a mixer such as, for example, a ribbon mixer, a Nauter mixer, a mixing granulator, or the like, to produce a powdered mixture in which the agricultural chemical technical product is adsorbed to the adsorbent carrier.

Next, the N-acylamino acid salt, and, wetting agents and other additives, if needed, are added to a pulverized product produced by pulverizing the obtained powdered mixture by means of a pin mill, a hammer mill, a ball mill, a jet mill, or the like, followed by mixing them by using the mixer described above. Water is added to the obtained mixture, followed by kneading, granulating, and then by drying the mixture, to produce a water dispersible granule. Before pulverizing the powdered mixture, a portion of, or all of the components excepting the agricultural chemical technical product and the adsorbent carrier may be mixed in advance with the mixture of the agricultural chemical technical product and the adsorbent carrier.

<Method of Producing the Water Dispersible Granule Using an Agricultural Chemical Technical Product Having Softening Point of 70° C. or Below>

When the water dispersible granule is produced by using an agricultural chemical technical product having softening point of 70° C. or below, both of the agricultural chemical technical product and the adsorbent carrier, or both of a solution in which the agricultural chemical technical product is dissolved in the above-mentioned volatile solvent or the above-mentioned nonvolatile solvent and the adsorbent carrier are mixed by using a mixer such as, for example, a ribbon mixer, a Nauter mixer, a mixing granulator, or the like, to produce a powdered mixture in which the solution is adsorbed to the adsorbent carrier. In the case of using the volatile solvent, the solvent is removed by heating after mixing by using a mixer such as a mixing granulator or the like, to produce the powdered mixture. In the case of using a nonvolatile solvent, it is used so that the adsorbent carrier adsorbing the agricultural chemical technical product is aggregated or powdered. After that, the mixture is pulverized by using a dry grinder such as a pin mill, a hammer mill, a ball mill, a jet mill, or the like. To the obtained pulverized product, the N-acylamino acid salt, and the wetting agent, if needed, and other additives are added, followed by mixing them by using the mixer described above. To the obtained mixture, water is added, followed by kneading, granulating, and then by drying the mixture in a manner similar to the above-mentioned producing method, to produce a water dispersible granule. As the pulverizing method used at that time, a method of extruding granulation, rolling granulation, mixing granulation, fluid bed granulation, spraying and drying granulation, pressing granulation, or the like may be used.

<Method of Using the Water Dispersible Granule>

According to the method of using the water dispersible granule of the present invention, after the water dispersible granule is put into water to be dispersed and diluted, it is applied to crops, soils, or the like, by using a sprayer or the like. Although the ratio of diluting the water dispersible granule with water may be varied in accordance with the variety, the content, or application targets of the agricultural chemical technical product contained in the water dispersible granule, the rate is generally approximately 1/10 to 1/10000, preferably approximately 1/50 to 1/8000, more preferably approximately 1/500 to 1/4000.

<Packing Form of the Water Dispersible Granule>

As the packing form of the water dispersible granule according to the present invention, containers which can be used for general granules or water dispersible granules, such as aluminum bags, paper bags, paper packs, polybottles, or the like may be used. In order to prevent moisture absorption during preservation, aluminum bags, or paper bags of which the inner portion is coated with aluminum, poly bags, or polybottles, or the like are preferable. It is also possible to prevent moisture absorption during preservation, to improve safety properties, and to improve handling properties during dilution, by packing the water dispersible granule in a water-soluble pack, followed by putting the pack in a bag treated to prevent moisture absorption.

As mentioned above, the present invention enables production of an agricultural and horticultural water dispersible granule which can satisfactorily disintegrate and disperse after it is put into water, even though an agricultural chemical technical product having a melting or softening point of 70° C. or below is used, which is conventionally difficult for use in a water dispersible granule. Because the N-acylamino acid salt used as the dispersant has low irritating properties effective on human body and low environmental toxicity, the water dispersible granule according to the present invention has high safety properties and no phytotoxic properties, and exerts stable effects on target pests.

EXAMPLES

In the following, the present invention will be explained in more detail with examples and comparative examples of the present invention, but the present invention should not be interpreted to be limited to these examples. In the following examples and comparative examples, "parts" and "%" respectively mean "parts by mass" and "% by mass", unless otherwise specified.

In the following, methods of measuring and evaluating are described.

(Disintegration Test in Water A)

250 ml of 53.6 ppm hard water based on official testing methods for agricultural chemicals was charged into a 250 ml stoppered messcylinder, and was then left in a thermostatic water bath at 20° C. Into the messcylinder, 500 mg of water dispersible granule was charged, and the disintegrability thereof was observed to evaluate it in the following five grades.

A: Most of the water dispersible granule was disintegrated before reaching the bottom of the messcylinder. The disintegrability was excellent.

B: The water dispersible granule was disintegrated in a condition between A and C. The disintegrability was approximately good.

C: The water dispersible granule was disintegrated while roping in water, or about 50 percent thereof was disintegrated before reaching the bottom of the messcylinder. The disintegrability was slightly good.

D: The water dispersible granules were disintegrated in a condition between C and E. The disintegrability was slightly unsatisfactory.

E: Most of the water dispersible granule reached the bottom of the messcylinder without being disintegrated. The disintegrability was unsatisfactory.
(Disintegration Test in Water B)

250 ml of 53.6 ppm hard water based on official testing methods for agricultural chemicals was charged into a 250 ml stoppered messcylinder, and was then left in a thermostatic water bath at 20° C. Into the messcylinder, 500 mg of water dispersible granule was charged. After one minute after that, the messcylinder was repeatedly turned over once per second, and the number of times required until the water dispersible granule was entirely disintegrated was measured to evaluate in accordance with the following grades.
(Disintegration Test in Water C)

This test was carried out by a method similar to that of the above-mentioned disintegration test in water A, except that CIPAC standard water D based on the CIPAC (Collaborative International Pesticide Analytical Council; Collaborative International Pesticide Analytical Council) method was used instead of 53.6 ppm hard water based on official testing methods for agricultural chemicals.
(Disintegration Test in Water D)

This test was carried out by a method similar to that of the above-mentioned disintegration test in water B, except that CIPAC standard water D based on the CIPAC (Collaborative International Pesticide Analytical Council; Collaborative International Pesticide Analytical Council) method was used instead of 53.6 ppm hard water based on official testing methods for agricultural chemicals.

The number of times of turnover was 0 to 4 times: Immediately disintegrated. Optimum.

The number of times of turnover was 5 to 9 times: Disintegrated in a condition still fit for practical use. Good.

The number of times of turnover was 10 to 14 times: Disintegration took a little time. Slightly inadequate.

The number of times of turnover was 15 to 19 times: Disintegration took a lot of time. Inadequate.

The number of times of turnover was 20 times or more: Not disintegrated. Inadequate.
(Suspensibility Test 1)

After the above-mentioned disintegration test in water B was carried out, the messcylinder was turned over a further 20 times. 5 minutes after that, the amount of deposits was visually observed, and was evaluated in accordance with the following grades.

○: The amount of the deposits was low. The suspensibility was excellent.

Δ: The amount of the deposits was slightly high. The suspensibility was slightly unsatisfactory.

X: The amount of the deposits was high. The suspensibility was unsatisfactory.
(Suspensibility Test 2)

After the above-mentioned disintegration test in water D was carried out, the messcylinder was turned over a further 20 times. 5 minutes after that, the amount of deposits was visually observed, and was evaluated in accordance with the following grades.

○: The amount of the deposits was low. The suspensibility was excellent.

Δ: The amount of the deposits was slightly high. The suspensibility was slightly unsatisfactory.

X: The amount of the deposits was high. The suspensibility was unsatisfactory.
(Dispersibility Test 1)

After the above-mentioned suspensibility test 1 was carried out, the messcylinder was turned over a further 2 to 3 times, and the dispersion was observed by using an optical microscope (400× magnification) to check for the existence of aggregation therein, and the powder was evaluated in accordance with the following grades.

○: Aggregation did not exist. The dispersibility was excellent.

Δ: A little aggregation existed. The dispersibility was slightly unsatisfactory.

X: Much aggregation existed. The dispersibility was unsatisfactory.
(Dispersibility Test 2)

After the above-mentioned suspensibility test 2 was carried out, the messcylinder was turned over a further 2 to 3 times, and the dispersion was observed by using an optical microscope (400× magnifications) to check for the existence of aggregation therein, and the powder was evaluated in accordance with the following grades.

○: Aggregation did not exist. The dispersibility was excellent.

Δ: A little aggregation existed. The dispersibility was slightly unsatisfactory.

X: Much aggregation existed. The dispersibility was unsatisfactory.
(Dispersibility Test 3)

After the above-mentioned dispersibility test 2 was carried out, the messcylinder was left still for 6 hours, and was then turned over a further 2 to 3 times. The dispersion was observed by using an optical microscope (400× magnifications) to check for the existence of aggregation therein, and the powder was evaluated in accordance with the following basis.

○: Aggregation did not exist. The dispersibility was excellent.

Δ: A little aggregation existed. The dispersibility was slightly unsatisfactory.

X: Much aggregation existed. The dispersibility was unsatisfactory.
(Measurement of Aqueous Dispersion Particle Diameter)

After the above-mentioned suspensibility test 1 was carried out, the messcylinder was turned over a further 2 to 3 times, and the average particle diameter (μm) of the dispersion was measured by using the particle size analyzer (manufactured by Coulter, Inc., LS 230). According to this evaluating method, a dispersion having a smaller average particle diameter is evaluated as one having a higher dispersibility (forming less aggregation) and thus being better.
(Observation of Oil Film Forming)

After the above-mentioned suspensibility test 1 was carried out, the condition of the water surface of the dispersion was visually observed to check for the existence of formed oil film, and was evaluated it in accordance with the following grades.

○: No formed oil film was observed, and homogeneous dispersion was observed. Excellent.

Δ: Although a small amount of formed oil film was observed, homogeneous dispersion was observed. Good.

X: Formed oil film was observed, and unhomogeneous dispersion was observed. Not good.
(Observation of Granulating Property)

The formability of granulated particles was visually observed, when granulation was carried out.

○: The granulating property was good, and desired granulated materials were produced.

X: The granulating property was too poor to carry out granulation, or the form after granulation could not be maintained.

Example 1

After 50 parts of iminoctadine albesilate (softening point: 60° C.) were dissolved in 50 parts of methanol, this solution was mixed with 50 parts of a synthetic noncrystalline silica (manufactured by SHIONOGI & CO., LTD., trade name "CARPLEX XR"), and was then heated to 50° C. to evaporate methanol. The produced powdered mixture was pulverized by using a jet mill (trade name "Super Sonic Jet Mill PJM" manufactured by Nippon Pneumatic Mfg. Co., Ltd.) to produce 100 parts of a powder containing 50% of iminoctadine albesilate.

60 parts of the produced powder containing 50% of iminoctadine albesilate, 20 parts of disodium N-stearoyl-L-glutamate (trade name "Amisoft HS-21" manufactured by AJINOMOTO Co., Inc.), 10 parts of sodium N-coconut oil fatty acid acyl-L-glutamate (trade name "Amisoft CS-11" manufactured by AJINOMOTO Co., Inc.), and 10 parts of diatomaceous earth (trade name "Zemlite 3Y" manufactured by Hakusan Corporation) were mixed together, and were then pulverized by using an "Sample Mill Type KII-1" (hammer mill manufactured by DALTON corporation) to produce a mixture having an average particle diameter of approximately 10 μm. The produced mixture was charged in a mixing granulator "Laboratorymatrix LMA5-V" (manufactured by NARA MACHINERY CO., LTD.), and was then granulated by mixing while dripping 15 parts of water to produce irregular shaped granules. The produced granules were dried at 45° C. for 3 hours, and were then subjected to sieving to produce a water dispersible granule having a particle size distribution range from 125 to 425 μm and containing 30% of iminoctadine albesilate as an active ingredient thereof.

Example 2

50 parts of dithiopyr (melting point: 65° C.) which is an agricultural chemical technical product pulverized in an approximate size from 0.1 to 20 mm, and 50 parts of diatomaceous earth ("Zemlite 3Y") were mixed together, and were then pulverized by using a "Super Sonic Jet Mill PJM". After the obtained pulverized material was left still at room temperature for 2 weeks, it was further pulverized by using an "Sample Mill Type KII-1" to produce a powder containing 50% of dithiopyr. 60 parts of the produced powder containing 50% of dithiopyr, 15 parts of disodium N-stearoyl-L-glutamate ("Amisoft HS-21"), 5 parts of sodium N-coconut oil fatty acid acyl-L-glutamate ("Amisoft CS-11"), and 20 parts of diatomaceous earth ("Zemlite 3Y") were mixed, and were then pulverized by using a pulverizer ("Type M20" manufactured by JANKE & KUNKEL GMBH & CO.KG) to produce a mixture having an average particle diameter of about 7 μm. The obtained mixture was charged in a kneader (trade name "small scale kneader type PNV-5" manufactured by IRIE Co., Ltd.), was kneaded while dripping 25 parts of water, and was then granulated using extruding granulator (trade name "TYPE KAR-180" manufactured by TSUTSUI RIKAGAKU KIKAI CO., LTD.) equipped with 0.5 mm. The obtained granules were dried at 45° C. for 3 hours, and were sieved to collect the water dispersible granules having a particle size distribution range from 180 to 1000 μm and containing 30% of dithiopyr as an active ingredient thereof.

Example 3

40 parts of benfuresate (melting point: 32 to 35° C.) which is an agricultural chemical technical product, 30 parts of diatomaceous earth (trade name "Zemlite 3Y"), and 30 parts of a synthetic noncrystalline silica (trade name "CARPLEX #1120" manufactured by SHIONOGI & CO., LTD.) were mixed together, and were then pulverized by using an "Sample Mill Type KII-1" to produce a powder containing 40% of benfuresate.

75 parts of the produced powder containing 40% of benfuresate, 12 parts of disodium N-stearoyl-L-glutamate ("Amisoft HS-21"), and 13 parts of sodium N-coconut oil fatty acid acyl-L-glutamate ("Amisoft CS-11") were mixed together, and were then pulverized by using the above-mentioned pulverizer to produce a mixture having an average particle diameter of about 10 lm. The obtained mixture was charged in a kneader ("small scale kneader type PNV-5"), was kneaded while dripping 25 parts of water, and was then granulated by extruding with a 0.5 mm screen of an extruding granulator (trade name "TYPE KAR-130"). The obtained granules were dried at 50° C. for 3 hours, and were then subjected to sieving to produce a water dispersible granule having a particle size distribution range from 180 to 1000 μm and containing 30% of benfuresate as an active ingredient thereof.

Example 4

60 parts of the powder, which was produced in Example 1, and which contained 50% of iminoctadine albesilate, 15 parts of disodium N-stearoyl-L-glutamate ("Amisoft HS-21"), 5 parts of diatomaceous earth ("Zemlite 3Y"), and 20 parts of partially desulfonated sodium lignosulfonate (trade name "VANILLEX N" manufactured by Nippon Paper Group, Inc.) were mixed together, and were then pulverized by using an "Sample Mill Type KII-1" to produce a mixture having an average particle diameter of about 10 μm. The obtained mixture was charged in a "Laboratorymatrix LMA5-V", and was then mixed while dripping 15 parts of water to produce irregular shaped granules. The obtained granules were dried at 45° C. for 3 hours, and were then subjected to sieving to produce a water dispersible granule having a particle size distribution range from 125 to 425 μm and containing 30% of iminoctadine albesilate as an active ingredient thereof.

Example 5

100 parts of a powder containing 50% of iminoctadine albesilate were produced in a manner similar to that of Example 1, except that a calcined synthetic noncrystalline silica (trade name "CARPLEX CS-7" manufactured by SHIONOGI & CO., LTD.) was used instead of the synthetic noncrystalline silica ("CARPLEX XR"). 60 parts of the produced powder containing 50% of iminoctadine albesilate, 15 parts of disodium N-stearoyl-L-glutamate ("Amisoft HS-21"), 5 parts of diatomaceous earth ("Zemlite 3Y"), and 20 parts of partially desulfonated sodium lignosulfonate ("VANILLEX N") were mixed together, and were then pulverized by using an "Sample Mill Type KII-1" to produce a mixture having an average particle diameter of about 10 μm. The obtained mixture was charged in a "Laboratorymatrix LMA5-V", and was then mixed while dripping 15 parts of water to produce irregular shaped granules. The obtained granules were dried at 45° C. for 3 hours, and were then subjected to sieving to produce a water dispersible granule having a particle size distribution range from 125 to 425 μm and containing 30% of iminoctadine albesilate as an active ingredient thereof.

Example 6

40 parts of the powder, which was produced in Example 1, and which contained 50% of iminoctadine albesilate, 30 parts of fenhexamid (melting point: 153° C.) which is an agricultural chemical technical product, 10 parts of disodium N-stearoyl-L-glutamate ("Amisoft HS-21"), 7 parts of sodium N-coconut oil fatty acid acyl-L-glutamate ("Amisoft CS-11"), and 13 parts of diatomaceous earth ("Zemlite 3Y") were mixed together, and were then pulverized by using an "Sample Mill Type KII-1" to produce a mixture having an average particle diameter of about 10 μm. The obtained mixture was charged in a "Laboratorymatrix LMA5-V", and was then mixed while dripping 12 parts of water to produce irregular shaped granules. The obtained granules were dried at 45° C. for 3 hours, and were then subjected to sieving to produce a water dispersible granule having a particle size distribution range from 150 to 425 μm and containing 20% of iminoctadine albesilate and 30% of fenhexamid as active ingredients thereof.

Example 7

40 parts of the powder, which was produced in Example 1, and which contained 50% of iminoctadine albesilate, 30 parts of fenhexamid (melting point: 153° C.) which is an agricultural chemical technical product, 15 parts of disodium N-stearoyl-L-glutamate ("Amisoft HS-21"), 2 parts of diatomaceous earth ("Zemlite 3Y"), and 13 parts of partially desulfonated sodium lignosulfonate ("VANILLEX N") were mixed together, and were then pulverized by using an "Sample Mill Type KII-1" to produce a mixture having an average particle diameter of about 10 μm. The obtained mixture was charged in a"Laboratorymatrix LMA5-V", and was then mixed while dripping 12 parts of water to produce irregular shaped granules. The obtained granules were dried at 45° C. for 3 hours, and were then subjected to sieving to produce a water dispersible granule having a particle size distribution range from 150 to 425 μm and containing 20% of iminoctadine albesilate and 30% of fenhexamid as active ingredients thereof.

Example 8

40 parts of the powder, which was produced in Example 1, and which contained 50% of iminoctadine albesilate, 30 parts of pyributicarb (melting point: 85.7 to 86.2° C.) which is an agricultural chemical technical product, 15 parts of disodium N-stearoyl-L-glutamate ("Amisoft HS-21"), and 15 parts of formaldehyde condensate of sodium aromatic sulfonate (trade name "DEMOL SNB" manufactured by Kao Corportaion) were mixed together, and were then pulverized by using the above-mentioned pulverizer to produce a mixture having an average particle diameter of about 10 μm. The obtained mixture was charged in a "Laboratorymatrix LMA5-V", and was then mixed while dripping 15 parts of water to produce irregular shaped granules. The obtained granules were dried at 45° C. for 3 hours, and were then subjected to sieving to produce a water dispersible granule having a particle size distribution range from 180 to 600 μm and containing 20% of iminoctadine albesilate and 30% of pyributicarb as active ingredients thereof.

Example 9

40 parts of the powder, which was produced in Example 1, and which contained 50% of iminoctadine albesilate, 30 parts of ipconazole (melting point: 91 to 119° C.) which is an agricultural chemical technical product, 15 parts of disodium N-stearoyl-L-glutamate ("Amisoft HS-21"), and 15 parts of partially desulfonated sodium lignosulfonate ("VANILLEX N") were mixed together, and were then pulverized by using an "Sample Mill Type KII-1" to produce a mixture having an average particle diameter of about 10 μm. The obtained mixture was charged in a "Laboratorymatrix LMA5-V", and was then mixed while dripping 12 parts of water to produce irregular shaped granules. The obtained granules were dried at 45° C. for 3 hours, and were then subjected to sieving to produce a water dispersible granule having a particle size distribution range from 180 to 600 μm and containing 20% of iminoctadine albesilate and 30% of ipconazole as active ingredients thereof.

Example 10

80 parts of the powder, which was produced in Example 2, and which contained 50% of dithiopyr, 15 parts of disodium N-stearoyl-L-glutamate ("Amisoft HS-21"), and 5 parts of partially desulfonated sodium lignosulfonate ("VANILLEX N") were mixed together, and were then pulverized by using the above-mentioned pulverizer to produce a mixture having an average particle diameter of about 7 μm. The obtained mixture was charged in a kneader ("small scale kneader type PNV-5"), was kneaded while dripping 25 parts of water, and was then granulated by extruding with a 0.5 mm screen of an extruding granulator (trade name "TYPE KAR-130"). The obtained granules were dried at 45° C. for 3 hours, and were then subjected to sieving to produce a water dispersible granule having a particle size distribution range from 180 to 1000 μm and containing 40% of dithiopyr as an active ingredient thereof.

Example 11

40 parts of benfuresate (melting point: 32 to 35° C.) which is an agricultural chemical technical product, and 60 parts of diatomaceous earth ("Zemlite 3Y") were mixed, and were then pulverized by using an "Sample Mill Type KII-1" to produce a powder containing 40% of benfuresate. 75 parts of the produced powder containing 40% of benfuresate, 8 parts of disodium N-stearoyl-L-glutamate ("Amisoft HS-21"), 7 parts of sodium N-coconut oil fatty acid acyl-L-glutamate ("Amisoft CS-11"), 5 parts of partially desulfonated sodium lignosulfonate ("VANILLEX N"), and 5 parts of diatomaceous earth ("Zemlite 3Y") were mixed together, and were then pulverized by using the above-mentioned pulverizer to produce a mixture having an average particle diameter of about 10 μm. The obtained mixture was charged in a "Laboratorymatrix LMA5-V", and was then mixed while dripping 15 parts of water to produce irregular shaped granules. The obtained granules were dried at 45° C. for 3 hours, and were then subjected to sieving to produce a water dispersible granule having a particle size distribution range from 180 to 600 μm and containing 30% of benfuresate as an active ingredient thereof.

Example 12

75 parts of the powder, which was produced in Example 11, and which contained 40% of benfuresate, 15 parts of sodium lauroyl sarcosine (trade name "Soypon SLP" manufactured by Kawaken Fine Chemicals Co., Ltd.), 5 parts of partially desulfonated sodium lignosulfonate ("VANILLEX N"), and 5 parts of diatomaceous earth ("Zemlite 3Y") were mixed together, and were then pulverized by using the above-mentioned pulverizer to produce a mixture having an average particle diameter of about 10 μm. The obtained mixture was charged in a "Laboratorymatrix LMA5-V", and was then mixed while dripping 15 parts of water to produce irregular shaped granules. The obtained granules were dried at 45° C. for 3 hours, and were then subjected to sieving to produce a water dispersible granule having a particle size distribution range from 180 to 600 μm and containing 30% of benfuresate as an active ingredient thereof.

Example 13

75 parts of the powder, which was produced in Example 3, and which contained 40% of benfuresate, 15 parts of sodium N-coconut oil fatty acid acyl-L-glutamate ("Amisoft CS-11"), and 10 parts of partially desulfonated sodium lignosulfonate ("VANILLEX N") were mixed together, and were then pulverized by using the above-mentioned pulverizer to produce a mixture having an average particle diameter of about 10 μm. The obtained mixture was charged in a kneader ("small scale kneader type PNV-5"), was kneaded while dripping 25 parts of water, and was then granulated by extruding with a 0.5 mm screen of an extruding granulator (trade name "TYPE KAR-130"). The obtained granules were dried at 50° C. for 3 hours, and were then subjected to sieving to produce a water dispersible granule having a particle size distribution range from 180 to 1000 μm and containing 30% of benfuresate as an active ingredient thereof.

Example 14

After a homogeneous solution consisting of 32 parts of benfuresate (melting point: 32 to 35° C.) which is an agricultural chemical technical product and 14 parts of a diluent for the agricultural chemical technical product "Hisol SAS-296" (a mixture containing a two-membered ring aromatic hydrocarbon compound manufactured by NIPPON PETROCHEMICALS COMPANY, LIMITED.) was mixed with 34 parts of a synthetic noncrystalline silica (trade name "CARPLEX #80" manufactured by SHIONOGI & CO., LTD.), and the mixture was pulverized by using an "Sample Mill Type KII-1" to produce a powder containing 40% of benfuresate.

80 parts of the produced powder containing 40% of benfuresate, 5 parts of sodium N-coconut oil fatty acid acyl-L-glutamate ("Amisoft CS-11"), 2 parts of sodium N-myristoyl methyl taurate (trade name "NIKKOL MMT" manufactured by Nikko Chemicals co., ltd.), 11 parts of bentonite as a filler, and 2 parts of sodium di-2-ethylhexyl sulfosuccinate as a wetting agent were mixed together, and were then pulverized by using the above-mentioned pulverizer to produce a mixture having an average particle diameter of about 10 μm. The obtained mixture was charged in a kneader ("small scale kneader type PNV-5"), was kneaded while dripping 25 parts of water, and was then granulated by extruding with a 0.5 mm screen of an extruding granulator ("TYPE KAR-130"). The obtained granules were dried at 50° C. for 3 hours, and were then subjected to sieving to produce a water dispersible granule having a particle size distribution range from 180 to 1000 μm and containing 30% of benfuresate as an active ingredient thereof.

Example 15

60 parts of the powder, which was produced in Example 1, and which contained 50% of iminoctadine albesilate, 12.5 parts of disodium N-stearoyl-L-glutamate ("Amisoft HS-21"), 2.5 parts of sodium N-myristoyl methyl taurate ("NIKKOL MMT"), 23 parts of modified sodium lignosulfonate (trade name "Perlex DP" manufactured by Nippon Paper Group, Inc.), and 2 parts of attapulgite were mixed together, and were then pulverized by using an "Sample Mill Type KII-1" to produce a mixture having an average particle diameter of about 10 μm. The obtained mixture was charged in a fluidizing granulator "Flow Coater FLO-1", was then sprayed with 80 parts of water while sending air to produce irregular shaped granules. After the obtained granules were dried at 50° C. for 3 hours, they were subjected to sieving to produce a water dispersible granule having a particle size distribution range from 125 to 1000 μm and containing 30% of iminoctadine albesilate as an active ingredient thereof.

Comparative Example 1

A water dispersible granule having a particle size distribution range from 125 to 425 μm and containing 30% of iminoctadine albesilate as an active ingredient thereof was produced in a manner similar to that of Example 1, except that partially desulfonated sodium lignosulfonate ("VANILLEX N") was used instead of disodium N-stearoyl-L-glutamate ("Amisoft HS-21") and sodium N-coconut oil fatty acid acyl-L-glutamate ("Amisoft CS-11").

Comparative Example 2

A water dispersible granule having a particle size distribution range from 180 to 1000 μm and containing 30% of dithiopyr as an active ingredient thereof was produced in a manner similar to that of Example 2, except that partially desulfonated sodium lignosulfonate ("VANILLEX N") was used instead of disodium N-stearoyl-L-glutamate ("Amisoft HS-21") and sodium N-coconut oil fatty acid acyl-L-glutamate ("Amisoft CS-11").

Comparative Example 3

A water dispersible granule having a particle size distribution range from 180 to 1000 μm and containing 30% of dithiopyr as an active ingredient thereof was produced in a manner similar to that of Example 3, except that partially desulfonated sodium lignosulfonate ("VANILLEX N") was used instead of disodium N-stearoyl-L-glutamate ("Amisoft HS-21") and sodium N-coconut oil fatty acid acyl-L-glutamate ("Amisoft CS-11").

Comparative Example 4

A water dispersible granule having a particle size distribution range from 125 to 425 μm and containing 30% of iminoctadine albesilate as an active ingredient thereof was produced in a manner similar to that of Example 4, except that partially desulfonated sodium lignosulfonate ("VANILLEX N") was used instead of disodium N-stearoyl-L-glutamate ("Amisoft HS-21").

Comparative Example 5

A water dispersible granule having a particle size distribution range from 125 to 425 μm and containing 30% of iminoctadine albesilate as an active ingredient thereof was produced in a manner similar to that of Example 4, except that sodium polycarboxylate (trade name "NEWKALGEN WG-5" manufactured by Takemoto Oil & Fat Co., Ltd.) was used instead of disodium N-stearoyl-L-glutamate ("Amisoft HS-21").

Comparative Example 6

A water dispersible granule having a particle size distribution range from 125 to 425 μm and containing 30% of iminoctadine albesilate as an active ingredient thereof was produced in a manner similar to that of Example 5, except that partially desulfonated sodium lignosulfonate ("VANILLEX N") was used instead of disodium N-stearoyl-L-glutamate ("Amisoft HS-21").

Comparative Example 7

A water dispersible granule having a particle size distribution range from 150 to 425 μm and containing 20% of iminoctadine albesilate and 30% of fenhexamid as an active ingredient thereof was produced in a manner similar to that of Example 6, except that a formaldehyde condensate of sodium aromatic sulfonate (trade name "DEMOL SNB" manufactured by Kao Corportaion) was used instead of disodium N-stearoyl-L-glutamate ("Amisoft HS-21") and sodium N-coconut oil fatty acid acyl-L-glutamate ("Amisoft CS-11").

Comparative Example 8

A water dispersible granule having a particle size distribution range from 180 to 600 μm and containing 20% of iminoctadine albesilate and 30% of pyributicarb as active ingredients thereof was produced in a manner similar to that of Example 8, except that a formaldehyde condensate of sodium aromatic sulfonate (trade name "DEMOL SNB" manufactured by Kao Corportaion) was used instead of disodium N-stearoyl-L-glutamate ("Amisoft HS-21").

Comparative Example 9

A water dispersible granule having a particle size distribution range from 180 to 600 μm and containing 20% of iminoctadine albesilate and 30% of ipconazole as active ingredients thereof was produced in a manner similar to that of Example 9, except that a formaldehyde condensate of sodium aromatic sulfonate (trade name "DEMOL SNB" manufactured by Kao Corportaion) was used instead of disodium N-stearoyl-L-glutamate ("Amisoft HS-21").

Comparative Example 10

A water dispersible granule having a particle size distribution range from 180 to 1000 μm and containing 40% of dithiopyr as an active ingredient thereof was produced in a manner similar to that of Example 10, except that a formaldehyde condensate of sodium aromatic sulfonate (trade name "DEMOL SNB") was used instead of disodium N-stearoyl-L-glutamate ("Amisoft HS-21").

Comparative Example 11

A water dispersible granule having a particle size distribution range from 180 to 1000 μm and containing 40% of dithiopyr as an active ingredient thereof was produced in a manner similar to that of Example 10, except that sodium polycarboxylate (trade name "NEWKALGEN WG-5" manufactured by Takemoto Oil & Fat Co., Ltd.) was used instead of disodium N-stearoyl-L-glutamate ("Amisoft HS-21").

Comparative Example 12

Preparation was carried out in a manner similar to that of Example 11, except that modified sodium lignosulfonate ("VANILLEX N") was used instead of disodium N-stearoyl-L-glutamate ("Amisoft HS-21") and sodium N-coconut oil fatty acid acyl-L-glutamate ("Amisoft CS-11"). As a result, a powdered water dispersible granule of which the form after granulation was easily lost, and which contained 30% of benfuresate as an active ingredient thereof was produced.

Comparative Example 13

Preparation was carried out in a manner similar to that of Example 11, except that a formaldehyde condensate of sodium aromatic sulfonate ("DEMOL SNB") was used instead of disodium N-stearoyl-L-glutamate ("Amisoft HS-21") and sodium N-coconut oil fatty acid acyl-L-glutamate ("Amisoft CS-11"). As a result, a powdered water dispersible granule of which the form after granulation was easily lost, and which contained 30% of benfuresate as an active ingredient thereof was produced.

Comparative Example 14

A water dispersible granule having a particle size distribution range from 180 to 1000 μm and containing 30% of benfuresate as an active ingredient thereof was produced in a manner similar to that of Example 13, except that a formaldehyde condensate of sodium aromatic sulfonate ("DEMOL SNB") was used instead of sodium N-coconut oil fatty acid acyl-L-glutamate ("Amisoft CS-11").

Comparative Example 15

60 parts of the powder, which was produced in Example 1, and which contained 50% of iminoctadine albesilate, were mixed with 10 parts of diatomaceous earth ("Zemlite 3Y"), onto which 115.5 parts of 26% of sodium dodecylbenzenesulfonate were sprayed, and were then mixed, to produce a kneaded material. The kneaded material was dried at 45° C. for 2 hours, and was then further mixed to produce irregular shaped granules. The obtained granules were dried at 45° C. for 3 hours, and were then subjected to sieving to produce a water dispersible granule having a particle size distribution range from 125 to 425 μm and containing 30% of iminoctadine albesilate as an active ingredient thereof.

Comparative Example 16

60 parts of the powder, which was produced in Example 2, and which contained 50% of dithiopyr, were mixed with 20 parts of diatomaceous earth ("Zemlite 3Y"), and were then pulverized by using a pulverizer ("Type M20"). The obtained mixture (having an average particle diameter of about 7 μm) was charged in a kneader ("small scale kneader type PNV-5"), was kneaded while dripping 77 parts of an aqueous solution containing 26% of sodium dodecylbenzenesulfonate, and was then granulated by extruding the kneaded material with a 0.5 mm screen of an extruding granulator ("TYPE KAR-180"). The obtained granules were dried at 45° C. for 3 hours, and were then subjected to sieving to produce a water dispersible granule having a particle size distribution range from 180 to 1000 μm and containing 30% of dithiopyr as an active ingredient thereof.

Comparative Example 17

80 parts of the powder, which was produced in Example 1, and which contained 50% of iminoctadine albesilate, 8 parts of polyoxyethylene dialkylphenyl ether sulfate ammonium salt, 8 parts of sodium laurylsulfate, and 9 parts of clay as a filler were mixed, and were then pulverized by using the above-mentioned pulverizer to produce a water dispersible granule containing 40% of iminoctadine albesilate as an active ingredient thereof.

thereof were unsatisfactory. Although the suspensibility and the dispersibility of the water dispersible granule produced in Comparative Example 15 were good, the underwater disinte-

TABLE 1

|  | Disintegration test in water A | Disintegration test in water B | Suspensibility test 1 | Dispersibility test 1 | Average particle diameter (μm) | Oil film formation | Granulating property |
|---|---|---|---|---|---|---|---|
| Example 1 | B | 9 times | ○ | ○ | 20.0 | ○ | ○ |
| Example 2 | A | 8 times | ○ | ○ | 18.0 | ○ | ○ |
| Example 3 | B | 5 times | ○ | ○ | 16.8 | ○ | ○ |
| Example 4 | B | 8 times | ○ | ○ | 17.5 | ○ | ○ |
| Example 5 | B | 9 times | ○ | ○ | 18.5 | ○ | ○ |
| Example 6 | B | 6 times | ○ | ○ | 21.0 | ○ | ○ |
| Example 7 | B | 7 times | ○ | ○ | 17.0 | ○ | ○ |
| Example 8 | B | 3 times | ○ | ○ | 14.9 | ○ | ○ |
| Example 9 | B | 6 times | ○ | ○ | 18.6 | ○ | ○ |
| Example 10 | A | 7 times | ○ | ○ | 7.6 | ○ | ○ |
| Example 11 | B | 2 times | ○ | ○ | 15.3 | ○ | ○ |
| Example 12 | B | 3 times | ○ | ○ | 11.6 | ○ | ○ |
| Example 13 | B | 3 times | ○ | ○ | 14.7 | ○ | ○ |
| Example 14 | B | 2 times | ○ | ○ | 11.5 | ○ | ○ |

As shown in Table 1, results in all characteristics of underwater disintegrability, suspensibility, and dispersibility of the water dispersible granules produced in Examples 1 to 14 were good or excellent.

grability thereof was unsatisfactory. The average particle diameter of the water dispersible granules, which were produced in Comparative Examples 1 to 14 and 16, and which were dispersed in water, was larger than that of the water

TABLE 2

|  | Disintegration test in water C | Disintegration test in water D | Suspensibility test 2 | Dispersibility test 2 | Dispersibility test 3 |
|---|---|---|---|---|---|
| Example 15 | A | 1 time | ○ | ○ | ○ |

As shown in Table 2, results in all characteristics of disintegrability under water having a high degree of hardness (CIPAC standard water D), suspensibility, and dispersibility of the water dispersible granule produced in Example 15 were good.

dispersible granules produced in the examples. This was probably because the water dispersible granules produced in Comparative Examples 1 to 14 and 16 were easily aggregated, and the surfactants thereof had insufficient dispersive ability.

TABLE 3

|  | Disintegration test in water A | Disintegration test in water B | Suspensibility test 1 | Dispersibility test 1 | Average particle diameter (μm) | Oil film formation | Granulating property |
|---|---|---|---|---|---|---|---|
| Comparative Example 1 | E | >20 times | X | X | 58.0 | ○ | ○ |
| Comparative Example 2 | E | >20 times | X | X | 65.0 | ○ | ○ |
| Comparative Example 3 | B | 4 times | Δ | Δ | 29.0 | ○ | ○ |
| Comparative Example 4 | E | >20 times | X | X | 58.0 | ○ | ○ |
| Comparative Example 5 | C | 6 times | Δ | Δ | 27.5 | ○ | ○ |
| Comparative Example 6 | E | >20 times | X | X | 63.5 | ○ | ○ |
| Comparative Example 7 | D | >20 times | X | X | 38.6 | ○ | ○ |
| Comparative Example 8 | C | 5 times | Δ | Δ | 25.2 | ○ | ○ |
| Comparative Example 9 | E | >20 times | X | X | 36.5 | ○ | ○ |
| Comparative Example 10 | E | >20 times | X | X | 68.0 | ○ | ○ |
| Comparative Example 11 | E | >20 times | X | X | 59.5 | ○ | ○ |
| Comparative Example 12 | B | 10 times | ○ | ○ | 20.9 | Δ | X |
| Comparative Example 13 | B | 3 times | ○ | ○ | 19.3 | Δ | X |
| Comparative Example 14 | B | 4 times | Δ | Δ | 37.0 | ○ | ○ |
| Comparative Example 15 | D | >20 times | ○ | ○ | 20.0 | ○ | ○ |
| Comparative Example 16 | E | >20 times | X | X | 98.0 | ○ | ○ |

As shown in Table 3, results in all characteristics of underwater disintegrability, suspensibility, and dispersibility of the water dispersible granules produced in Comparative Examples 1, 2, 4, 6, 7, 9 to 11, and 16 were unsatisfactory. Results of suspensibility and dispersibility of the water dispersible granules produced in Comparative Examples 3, 5, 8, and 14 were slightly unsatisfactory. Although the underwater disintegrability, the suspensibility, and the dispersibility of the water dispersible granules produced in Comparative Examples 12 and 13 were good, the granulating properties <Biological Effect Test>

6 cucumber plants (variety: Top Green) conventionally cultivated in a section of 1×1.5 m in a greenhouse were used for each agent. Each agent produced in Example 4 and Comparative Example 17 was diluted with water to adjust the content of active ingredients thereof to respective values shown in the following table, and was then sprayed twice per week in satisfactory amounts (equivalent to 300 1/10a) onto the cucumbers at the 10th leaf stage at the beginning of this test by using a backpack type power sprayer. 18 days after application for the last time, the condition of all plants cultivated at each section was checked by using 10 true leaves grown at the sixth or higher position from the bottom, and the preventive value thereof was calculated from the rate of diseased leaves and the disease degree thereof in accordance with using the following formula 2. Existence of phytotoxicity was properly checked with naked eyes.

(Disease index)

0: No disease was observed.
5: Slight disease was observed.
1: The rate of diseased area was below 5%.
2: The rate of diseased area was no less than 5% and less than 25%.
3: The rate of diseased area was no less than 25% and less than 50%.
4: The rate of diseased area was no less than 50%.

Disease degree=Σ(the numbers of leaves at each disease index×the disease index)×100÷(the total number of checked leaves×4)  (Formula 1)

Preventive value=(the disease degree of an untreated control−the disease degree of the treated section)×100÷the disease degree of the untreated control  (Formula 2)

TABLE 4

| | Dilution rate (concentration) | Rate of diseased leaves | Disease degree | Preventive value | Existence of phytotoxicity |
|---|---|---|---|---|---|
| Example 4 | 2000 fold (150 mg/L) | 2.4 | 0.3 | 99.5 | none |
| | 4000 fold (75 mg/L) | 10.4 | 1.5 | 97.3 | none |
| Comparative Example 17 | 2000 fold (150 mg/L) | 0.6 | 0.1 | 99.8 | none |
| | 4000 fold (75 mg/L) | 12.1 | 2.0 | 96.3 | none |
| Untreated control | — | 100.0 | 53.6 | — | none |

As shown in Table 4, it is apparent that the water dispersible granule produced in Example 4 exerted preventive effects equivalent to that of the water dispersible granule produced in Comparative Example 17 and did not exert phototoxic effects.

Although some preferable embodiments of the present invention are described in the above, these are merely representative examples, and should not be interpreted as limiting. It is possible that additions, omissions, substitutions, and other changes can be made without departing from the sprit or the scope of the present invention. Accordingly, the present invention should not be interpreted to be limited to the above description, and should be interpreted to be limited only by the appended claims.

INDUSTRIAL APPLICABILITY

The agricultural and horticultural water dispersible granule according to the present invention exerts excellent underwater disintegrability and dispersibility made possible by using the salt of N-acylamino acid as a dispersant, even though it contains an agricultural chemical technical product having a melting or softening point of 70° C. or below, which is conventionally difficult for use in water dispersible granules.

The agricultural and horticultural water dispersible granule according to the present invention has reduced toxicity effects on humans and the environment, because the agricultural chemical technical product contained as an active ingredient takes effect stably without causing phytotoxicity, and the acid of N-acylamino used as a dispersant has low properties of irritating the human body or animals, and is decomposed in the natural enviroment.

The agricultural and horticultural water dispersible granule according to the present invention exerts excellent underwater disintegrability and dispersibility which is made possibleby further containing N-acylmethyltaurate, even if it is applied to hard water containing a great deal of Ca or Mg.

The invention claimed is:

1. An agricultural and horticultural water dispersible granule comprising an agricultural chemical compound, a salt of N-acylamino acid that has an acyl group having 8 to 24 carbon atoms, and an adsorbent carrier selected from the group consisting of synthetic noncrystalline silicas and diatomaceous earth;
  wherein the agricultural chemical compound consists of at least one compound having a melting or softening point of 70° C. or below.

2. An agricultural and horticultural water dispersible granule according to claim 1, wherein the salt of N-acylamino acid is a salt of N-acylated material of at least one amino acid selected from the group consisting of glycine, sarcosine, alanine, valine, leucine, lysine, arginine, glutamic acid, aspartic acid, methionine, cystine, cysteine, and phenylalanine.

3. An agricultural and horticultural water dispersible granule according to claim 1, wherein the agricultural chemical compound contains as its main component at least one selected from the group consisting of dimethametryn, dithiopyr, benfuresate, cyhalofop-butyl, dimepiperate, pretilachlor, esprocarb, and iminoctadine albesilate.

4. An agricultural and horticultural water dispersible granule according to claim 1, wherein 10 to 60% by mass of the agricultural chemical compound, 10 to 30% by mass of the N-acylamino acid, and 10 to 80% by mass is the adsorbent carrier.

5. An agricultural and horticultural water dispersible granule according to claim 1, further comprising at least one selected from the group consisting of formaldehyde condensates of aromatic sulfonates and lignosulfonates.

6. An agricultural and horticultural water dispersible granule according to claim 5, wherein the ratio of the at least one selected from the group consisting of formaldehyde condensates of aromatic sulfonates and lignosulfonates is 5 to 25% by mass relative to a total mass of the agricultural chemical compound, the N-acylamino acid, the adsorbent carrier, and the at least one selected from the group consisting of formaldehyde condensates of aromatic sulfonates and lignosulfonates.

7. An agricultural and horticultural water dispersible granule according to claim 1, further comprising an N-acylmethyltaurate.

8. An agricultural and horticultural water dispersible granule according to claim 7, wherein the N-acylmethyltaurate has an acyl group having 8 to 24 carbon atoms.

9. An agricultural and horticultural water dispersible granule according to claim 7, wherein the ratio of N-acylmethyltaurate is 0.5 to 10% by mass relative to a total mass of the agricultural chemical compound, the N-acylamino acid, the adsorbent carrier, and the N-acylmethyltaurate.

10. An agricultural and horticultural water dispersible granule according to claim 5, further comprising an N-acylmethyltaurate.

11. An agricultural and horticultural water dispersible granule according to claim 10, wherein the N-acylmethyltaurate has an acyl group having 8 to 24 carbon atoms.

12. An agricultural and horticultural water dispersible granule according to claim 10, wherein the ratio of N-acylmethtaurate is 0.5 to 10% by mass relative to a total mass of the agricultural chemical compound, the N-acylamino acid, the adsorbent carrier, the at least one selected from the group consisting of formaldehyde condensates of aromatic sulfonates and lignosulfonates, and the N-acylmethyltaurate.

* * * * *